US008303613B2

(12) United States Patent
Crandall et al.

(10) Patent No.: US 8,303,613 B2

(45) Date of Patent: Nov. 6, 2012

(54) ULTRASONIC INSTRUMENT USING LANGEVIN TYPE TRANSDUCERS TO CREATE TRANSVERSE MOTION

(75) Inventors: Frank Anthony Crandall, Salt Lake City, UT (US); Blake Allen, Murray, UT (US); Mark Stringham, Kearns, UT (US); Joseph Luis, West Valley City, UT (US); Olga Jovic, Midvale, UT (US); David Blaine, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 532 days.

(21) Appl. No.: 12/329,314

(22) Filed: Dec. 5, 2008

(65) Prior Publication Data

US 2009/0149801 A1 Jun. 11, 2009

Related U.S. Application Data

(60) Provisional application No. 61/012,239, filed on Dec. 7, 2007.

(51) Int. Cl.
*A61B 17/32* (2006.01)

(52) U.S. Cl. .................. 606/171; 310/325; 310/323.12; 310/323.01; 310/323.02; 310/323.19; 310/365; 310/366

(58) Field of Classification Search .................. 606/171, 606/107, 161, 39, 167, 169, 22; 604/22, 604/272; 600/437; 601/2; 310/323.12, 325, 310/328, 366, 317
See application file for complete search history.

(56) References Cited

U.S. PATENT DOCUMENTS 2,704,333 A 3/1955 Calosi et al.
2,974,296 A * 3/1961 Rosen .......................... 333/187
3,090,222 A 5/1963 Akaboshi et al.
3,450,476 A 6/1969 Rando
3,588,859 A 6/1971 Petree
3,689,783 A 9/1972 Williams
3,694,675 A 9/1972 Loveday
3,805,787 A 4/1974 Banko
3,939,360 A 2/1976 Jackson
3,974,681 A 8/1976 Namery
3,987,674 A 10/1976 Baumoel
4,002,996 A 1/1977 Kebanoff et al.
4,032,803 A 6/1977 Durr et al.
4,083,038 A 4/1978 Kebanoff
4,144,517 A 3/1979 Baumoel
(Continued)

FOREIGN PATENT DOCUMENTS

DE 3241033 5/1984
(Continued)

OTHER PUBLICATIONS

International Search Report and The Written Opinion for Related Application, Feb. 3, 2009.

*Primary Examiner* — Ryan Severson
*Assistant Examiner* — Rachel S Papeika
(74) *Attorney, Agent, or Firm* — Hodgson Russ LLP

(57) ABSTRACT

A Langevin transducer horn uses split electroding or selective electroding of transducer elements and phase relationships of the voltages applied thereto to determine the relative longitudinal and flexural/transverse motion induced in the tip of the horn.

21 Claims, 3 Drawing Sheets

U.S. PATENT DOCUMENTS 4,169,984 A 10/1979 Parisi et al.
4,183,007 A 1/1980 Baird
4,193,004 A 3/1980 Lobdell et al.
4,280,126 A 7/1981 White
4,312,341 A 1/1982 Zissimopoulos et al.
4,316,465 A 2/1982 Dotson
4,559,454 A 12/1985 Kramer
4,577,629 A 3/1986 Martinez
4,580,448 A 4/1986 Skrgatic
4,631,529 A 12/1986 Zeitz
4,663,965 A 5/1987 Metcalf et al.
4,749,988 A 6/1988 Berman et al.
4,753,234 A 6/1988 Martinez
4,804,364 A 2/1989 Dieras
4,821,558 A 4/1989 Pastrone et al.
4,829,448 A 5/1989 Balding et al.
4,833,918 A 5/1989 Jean et al.
4,838,853 A 6/1989 Parisi
4,861,332 A 8/1989 Parsi
4,870,953 A 10/1989 DonMicheal et al.
4,881,487 A 11/1989 Moore
4,884,065 A 11/1989 Crouse et al.
4,896,099 A 1/1990 Suzuki
4,897,079 A 1/1990 Zaleski et al.
4,908,676 A 3/1990 Bedell et al.
4,920,336 A 4/1990 Meijer
4,931,047 A 6/1990 Broadwin
4,979,952 A 12/1990 Kubota et al.
4,983,901 A 1/1991 Lehmer
4,998,022 A 3/1991 Tregay
5,011,471 A 4/1991 Miyazaki et al.
5,015,227 A 5/1991 Broadwin
5,026,387 A 6/1991 Thomas
5,037,386 A 8/1991 Marcus et al.
5,053,747 A 10/1991 Slate et al.
5,074,659 A 12/1991 Suzuki et al.
5,098,387 A 3/1992 Wiest et al.
5,112,300 A 5/1992 Ureche
5,116,759 A 5/1992 Klainer et al.
5,121,628 A 6/1992 Merkl et al.
5,123,903 A 6/1992 Quaid et al.
5,160,317 A 11/1992 Costin
5,178,605 A 1/1993 Imonti
5,180,363 A 1/1993 Idemoto et al.
5,182,947 A 2/1993 Fidelak et al.
5,190,517 A 3/1993 Zieve et al.
5,236,414 A 8/1993 Takasu
5,260,665 A 11/1993 Goldberg et al.
5,261,883 A 11/1993 Hood et al.
5,268,624 A 12/1993 Zanger
5,278,471 A * 1/1994 Uehara et al. ................ 310/328
5,295,120 A 3/1994 McShane
5,303,585 A 4/1994 Lichte
5,305,237 A 4/1994 Dalrymple et al.
5,331,951 A 7/1994 Kepley
5,344,420 A 9/1994 Hilal et al.
5,370,602 A 12/1994 Kepley
5,388,569 A 2/1995 Kepley
5,413,556 A 5/1995 Whittingham et al.
5,417,672 A 5/1995 Nita et al.
5,438,868 A 8/1995 Holden et al.
5,442,495 A 8/1995 Saito et al.
5,449,370 A 9/1995 Vaitekunas
5,453,087 A 9/1995 Malinowski
5,456,887 A 10/1995 Calvo et al.
5,472,447 A 12/1995 Abrams et al.
5,499,077 A 3/1996 Endo et al.
5,514,087 A 5/1996 Jones
5,514,102 A 5/1996 Winterer et al.
5,534,708 A 7/1996 Ellinger et al.
5,554,894 A 9/1996 Sepielli
5,557,368 A 9/1996 Endo et al.
5,562,610 A 10/1996 Brumbach
5,649,935 A 7/1997 Kremer et al.
5,672,887 A 9/1997 Shaw et al.
5,680,111 A 10/1997 Danby et al.
5,728,130 A 3/1998 Ishikawa et al.
5,746,756 A 5/1998 Bromfield et al.
5,764,356 A 6/1998 Iwase et al.
5,798,050 A 8/1998 Gaynes et al.
5,814,922 A * 9/1998 Uchino et al. ................ 310/359
5,843,109 A 12/1998 Mehta et al.
5,844,587 A 12/1998 Ando et al.
5,879,364 A 3/1999 Bromfield et al.
5,921,999 A * 7/1999 Dileo ........................... 606/166
5,983,749 A 11/1999 Holtorf
6,064,577 A 5/2000 Moskowitz et al.
6,068,612 A 5/2000 Bowman et al.
6,069,433 A 5/2000 Lazarus et al.
6,142,008 A 11/2000 Cole et al.
6,150,623 A 11/2000 Chen
6,179,829 B1 1/2001 Bisch
6,251,113 B1 6/2001 Appelbaum et al.
6,260,434 B1 7/2001 Holtorf
6,346,764 B1 * 2/2002 Boyd ........................... 310/366
6,360,630 B2 3/2002 Holtorf
6,452,123 B1 9/2002 Chen
6,478,766 B1 11/2002 Chon
6,531,708 B1 3/2003 Malmstrom et al.
6,543,885 B2 4/2003 Bahl et al.
6,602,193 B2 8/2003 Chon
6,674,030 B2 1/2004 Chen et al.
6,709,392 B1 3/2004 Salgo et al.
6,740,058 B2 5/2004 Lal et al.
6,750,468 B2 6/2004 Malmstrom et al.
6,852,092 B2 2/2005 Kadziauskas et al.
6,921,385 B2 * 7/2005 Clements et al. ............. 604/141
6,932,114 B2 8/2005 Sparks
7,012,203 B2 3/2006 Hanson et al.
7,152,482 B2 12/2006 Ueno et al.
7,169,123 B2 1/2007 Kadziauskas et al.
7,470,277 B2 12/2008 Finlay et al.
2002/0138080 A1 9/2002 Chon
2002/0161326 A1 10/2002 Sussman
2002/0192111 A1 12/2002 Divino, Jr. et al.
2002/0193817 A1 12/2002 Lal et al.
2003/0055375 A1 3/2003 Holst et al.
2003/0073980 A1 4/2003 Finlay et al.
2004/0019318 A1 1/2004 Wilson et al.
2004/0024412 A1 2/2004 Clements
2004/0092922 A1 5/2004 Kadziauskas et al.
2004/0197223 A1 10/2004 Olsen et al.
2005/0228423 A1 10/2005 Khashayar et al.
2005/0228424 A1 10/2005 Khashayar et al.
2005/0234407 A1 10/2005 Spohn et al.
2006/0036180 A1 2/2006 Boukhny et al.
2006/0145540 A1 7/2006 Mezhinsky
2006/0219049 A1 10/2006 Horvath et al.
2008/0281253 A1 11/2008 Injev et al.
2008/0294087 A1 11/2008 Steen et al.
2009/0005712 A1 1/2009 Raney
2010/0069825 A1 3/2010 Raney
2010/0069828 A1 3/2010 Steen et al.

FOREIGN PATENT DOCUMENTS

EP 1 704 839 9/2006
GB 2249419 5/1992
JP 61 3012 1/1986
JP 61-3012 1/1986
SU 1388002 4/1988
WO WO 2008060859 5/2008
WO WO 2008/147771 12/2008
WO WO 2010/014937 2/2010
WO WO 2010/014942 2/2010

* cited by examiner

ULTRASONIC INSTRUMENT USING LANGEVIN TYPE TRANSDUCERS TO CREATE TRANSVERSE MOTION

RELATED APPLICATIONS

The present application claims the benefit of U.S. Provisional Application Ser. No. 61/012,239, filed Dec. 7, 2007, which is expressly incorporated herein by reference in its entirety.

BACKGROUND OF THE INVENTION

1. The Field of the Invention

The present invention relates to inducing transverse motion at the end of a needle attached to a Langevin transducer horn. More specifically, the present invention relates to an improved Langevin transducer that induces transverse motion along with longitudinal motion.

2. State of the Art

Cataracts are the leading cause of blindness in the world. It is estimated that in the United States, age-related lenticular changes have been reported in 42% of those between 52 and 64, 60% of people between 65 and 74 and 91% of people between 75 and 85. A cataract is an opacity or cloudiness in the lens of the eye.

To address these issues, it has been common for a number of years to remove the lens of the eye. Initially this was done by making a large incision to facilitate removal of the lens and in some cases, replacing the lens with an implant.

In modern cataract surgery, phacoemulsification is a common procedure to facilitate removal of the damaged lens. Phacoemulsification involves using an ultrasonic handpiece to emulsify the cataract in the eye while the eye is irrigated with a balanced salt solution. The emulsified lens is aspirated and a prosthetic intraocular lens implant is inserted where the original lens was. This procedure has substantially reduced the size of the incision necessary in the eye and has significantly reduced recuperation time for patients.

In a conventional phacoemulsification handpiece, a hollow, resonating horn and a hollow needle attached thereto are disposed in communication with an aspirating line which suctions emulsified material through the center of the horn. The horn is disposed in a housing which typically includes an irrigation portion for introducing fluid around the horn and into the patient's eye.

A number of piezoelectric elements (often ceramic piezoelectric elements), typically referred to as a stack, are disposed adjacent each other about the horn. When the piezoelectric stack is subjected to an oscillating voltage, the ceramic piezoelectric elements expand and contract, thereby causing rapid longitudinal movement (i.e. longitudinal vibration at ultrasonic frequencies) in the horn and thereby in a needle which is attached at a distal end of the horn. The longitudinal vibration is used to emulsify the cataractous lens, allowing the cataract to be removed.

It is believed that transverse motion of the hand piece tip aids in phacoemulsification. There have been numerous attempts to create transverse motion during tissue removal. See e.g. U.S. Pat. No. 6,402,769 (Boukhny et al); U.S. Pat. No. 5,722,945 (Anis et al.); U.S. Pat. No. 5,222,959 (Anis et al); U.S. Pat. No. 4,504,264 (Kelman); and U.S. Patent Pub. 2006/0041220. In order to achieve out-of-plane motion in the horn, other inventors have created torsional motion in the horn and converted the torsional motion to transverse motion via a special bent needle. This torsional motion may be created through a separate ceramic stack, a configuration creating torsional motion with the stack or through slits made in the horn which change the geometry of the transducer. These methods introduce mechanical loss through conversion of torsional motion to transverse motion and appear to increase costs, and require the use of a bent needle to convert the torsional motion to a transverse motion. Furthermore, each requires changes to conventional handpiece design.

Thus, there is a need for a method for producing transverse movement in the horn and/or a needle attached to a horn. Preferably, such a method should be relatively low cost, not require major changes to existing handpiece design, and work with existing needles.

SUMMARY OF THE INVENTION

It is an object of the present invention to provide an improved Langevin transducer that induces transverse motion along with longitudinal motion.

According to one aspect of the invention, transverse motion is induced in the tip of a Langevin horn by split electrodes on the face of ceramic elements. More specifically, out of phase voltage signals are applied to the split electrodes, inducing out of phase strain in the material. This out of phase strain creates flexural motion in the horn. More specifically, when the voltage signals applied to the split electrodes are 180 degrees out of phase, one side of the transducer expands while the opposing side contracts. This induces flexural motion in the horn, creating transverse (lateral) motion at the end of the needle. When the applied voltage signals are in phase, longitudinal motion is induced in the horn. Thus, a Langevin transducer can provide both longitudinal and transverse motion without changing the geometry of the transducer stack and without adding a dedicated transducer for creating flexural or other transverse motion.

According to another aspect of the invention, transverse motion and longitudinal motion are induced at the tip of the Langevin horn by selectively applying voltage to selected opposing sides of transducers along the stack. By regulating the application of voltage to the various crystals, both longitudinal and transverse motion can be controlled.

According to another aspect of the invention, the amount of flexural motion (and thus transverse motion at the end of the needle) versus longitudinal motion is adjustable according to the voltage phase between the voltage signals applied to the crystals.

According to another aspect of the invention, the ceramic electrodes may be segmented into 3 or more isolated conductors. By regulating the phase of the drive signal to the conductors various different types of motion may be induced in the horn, and thus in the tip of the needle attached to the horn.

These and other aspects of the present invention are realized in an improved Langevin transducer that induces transverse motion due to flexural mode of the handpiece along with longitudinal motion as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it may not be possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
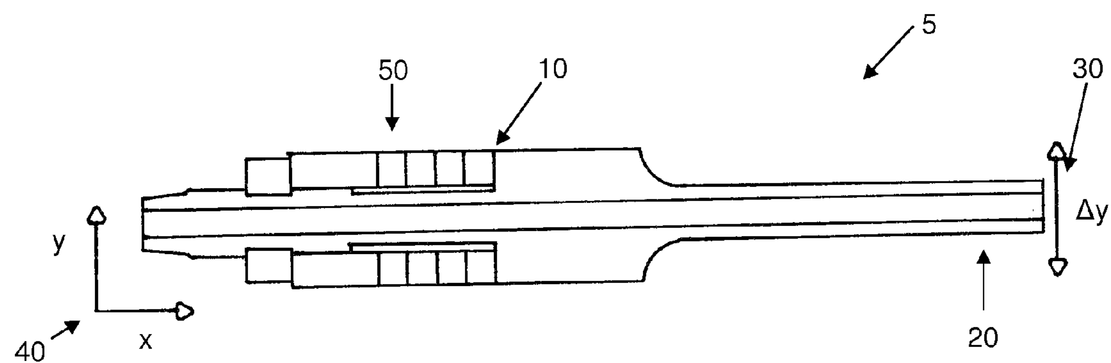
FIG. 1 shows a cross-section of a phacoemulsification horn with Langevin transducers and indicates a coordinate frame of reference.

Turning now to FIG. 1, a cross section of a phacoemulsification horn 5 is shown. In normal use, the horn 5 would be disposed inside of a handpiece and would thus have a housing disposed about it for grasping by a surgeon. A needle would be attached at the right end of the horn 5, and an aspiration tube would be attached at the opposing end. The use of such phacoemulsification handpieces is well known and is therefore not specifically shown in FIG. 1.

Disposed about the horn 5 are a number of transducer elements 10 disposed in a stack 50. As discussed herein, the transducer elements are typically, though not necessarily, a flat, annular, piece of piezoelectric ceramic, and an oscillating voltage potential is applied to the opposing faces of the ceramic element in order to cause oscillating expansion and contraction of the ceramic element. In a conventional stack of transducer elements 10, the transducer elements would be subject to an oscillating voltage 10. This would cause expansion and contraction of the transducer elements 10 and cause longitudinal movement of the horn 5 along the X axis as designated by the reference coordinates indicated at 40.

According to the present invention, it has been found that the same basic stack geometry can be used to create transverse (lateral) motion of the tip of a phacoemulsification needle, i.e. transverse oscillating motion in the Y axis—designated at 30—due to the formation of flexural motion of the horn. Unlike prior art attempts, special stack geometries and/or slits to promote torsional motion are not required. Thus a conventional horn, a conventional handpiece and a conventional needle can still be used while producing a lateral oscillation of the needle tip by using a transducer stack as shown in the present invention.

According to the present invention, a transducer stack 50 is provided which allows for both longitudinal and lateral motion of the needle tip by selecting the manner in which electricity is applied to the transducer stack. The phase relationship of the oscillating voltage applied to different portions of the transducer stack 50 allows for a choice of flexural (transverse) and/or longitudinal oscillation of the needle tip. According to a preferred stack configuration, if in phase oscillating voltages are applied to the transducer stack 50, the tip 20 of the horn 5 will oscillate longitudinally in the X direction while if 180 degrees out of phase oscillating voltages are applied to opposing sides of the transducer elements 10, one side of the transducer elements will expand while the other side contracts. The uneven expansion and contraction causes the tip 20 of the horn 10 to oscillate transversely as shown at 30, thereby creating transverse motion.

Should out of phase oscillating voltages be applied that are out of phase by an angle other than 180 degrees, the tip 20 can be made to oscillate both longitudinally and transversely 30. The phase relationship determines the amount of relative flexural/transverse and longitudinal oscillation. Phase relationships closer to 0 will oscillate more in the longitudinal direction, while phase relationships closer to 180 will oscillate more in the flexural direction.

Figure 2:
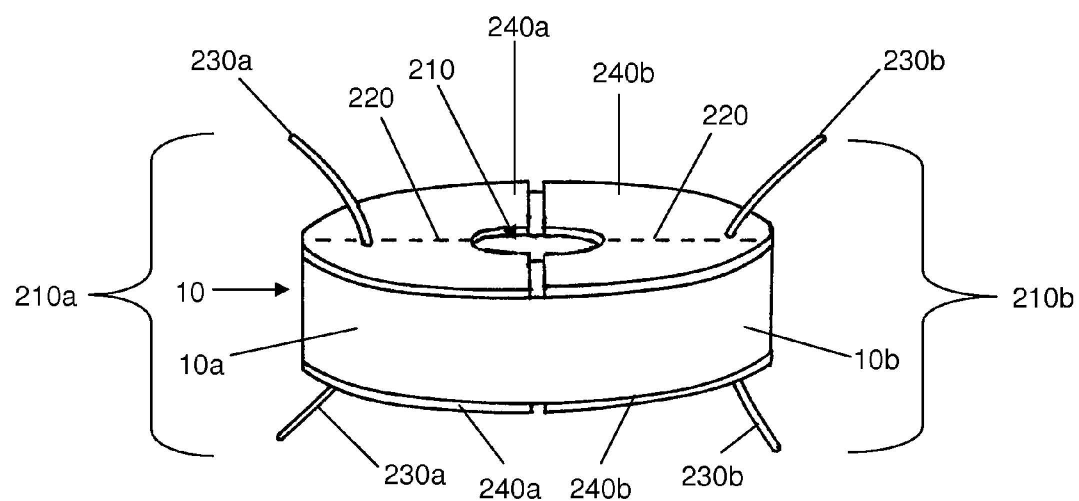
FIG. 2 shows a perspective view of a Langevin transducer element in accordance with the invention.

Turning to FIG. 2, a perspective view of a single piezoelectric transducer element 10 is shown in accordance with the invention. The transducer element 10 is typically a flat annular shape, the horn passing through the hole 210 in the transducer element. Typically, the two flat opposed sides of the ceramic disc are coated with a metal such as silver to thereby form electrodes, i.e. electrical contacts, on the two sides of the ceramic element. The electrical potential between the two sides of the ceramic material causes the physical expansion of the material. According to one aspect of the present invention, the two halves of the transducer element 10 are electrically insulated from one another. Each transducer element portion **10*a*, 10*b* has one or more electrodes 240*a*, 240*b* and corresponding electrical leads 230*a*, 230*b* attached thereto, through which a different voltage 210*a*, 210*b* may be applied. Dividing the piezoelectric element into separate regions allows a different (oscillating) voltage potential to be applied to each region to thereby alter the motion of the needle tip. For example, a larger voltage potential may be applied to one side 10*a* of the piezoelectric element 10 than is applied to the other side 10*b*, causing side 10*a* to expand more than side 10*b*. Alternatively, the voltages may be applied out of phase to the sides of the piezoelectric element 10, such as applying the opposite voltage polarity to side 10*b* as compared to side 10*a* (an oscillating voltage which is 180 degrees out of phase) such that side 10*a* expands while side 10*b*** contracts and vice versa.

The transducer element 10 may also be divided into more than two electrically isolated portions, as indicated by dashed lines 220. Typically, the transducer element 10 would be divided radially into symmetrical active regions (such as pie shaped wedges). Thus, the transducer element could be divided into 3, 4, or more active regions, each having separate electrodes 240 and electrical leads 230. Having 3 or 4 different active regions may allow for other types of motion to be produced at the phacoemulsification needle, depending on how the transducer element regions are driven. Although FIG. 2 shows a unitary piece of ceramic with electrically isolated electrodes 240, the ceramic may also be divided into separate pieces for each electrically isolated portion of the transducer element 10.

According to a preferred method of driving the piezoelectric elements 10, a wave form voltage potential (such as a sinusoidal or a square wave) is applied to the ceramic elements, and the wave form may be phase shifted between different halves of one or more ceramic elements to cause differing expansion of the ceramic element. When the plurality of oscillating voltages 210 are in phase between the two halves, the corresponding portions of the transducer 10 expand and contract in phase, producing longitudinal oscillations. When the plurality of oscillating voltages are out of phase, the corresponding portions 10*a* and 10*b* of the transducer expand and contract out of phase, causing out of phase movement of the portions 10*a* and 10*b* of the transducer and inducing a bending of the horn. The bending of the horn provides flexural oscillation.

It will be appreciated that, by controlling the phase, the relative longitudinal motion to transverse motion can be controlled. Thus, a surgeon could, in real time, adjust the ratio of longitudinal and transverse motion being produced in the horn to better accommodate the particularities or the surgery or the simple preferences of the surgeon. Additionally, such control is accomplished without requiring special transducer configurations or stacks dedicated to creating torsional motion.

As an alternative to the transducer element shown in FIG. 2, a transducer element may be made of two discrete halves 10*a* and 10*b* rather than one piece of ceramic with electrically separated electrodes 240. Additionally, one half 10*a* may be an active ceramic element and the other half (such as 10*b*) may be a non piezoelectric ceramic such as alumina.

Figure 3:
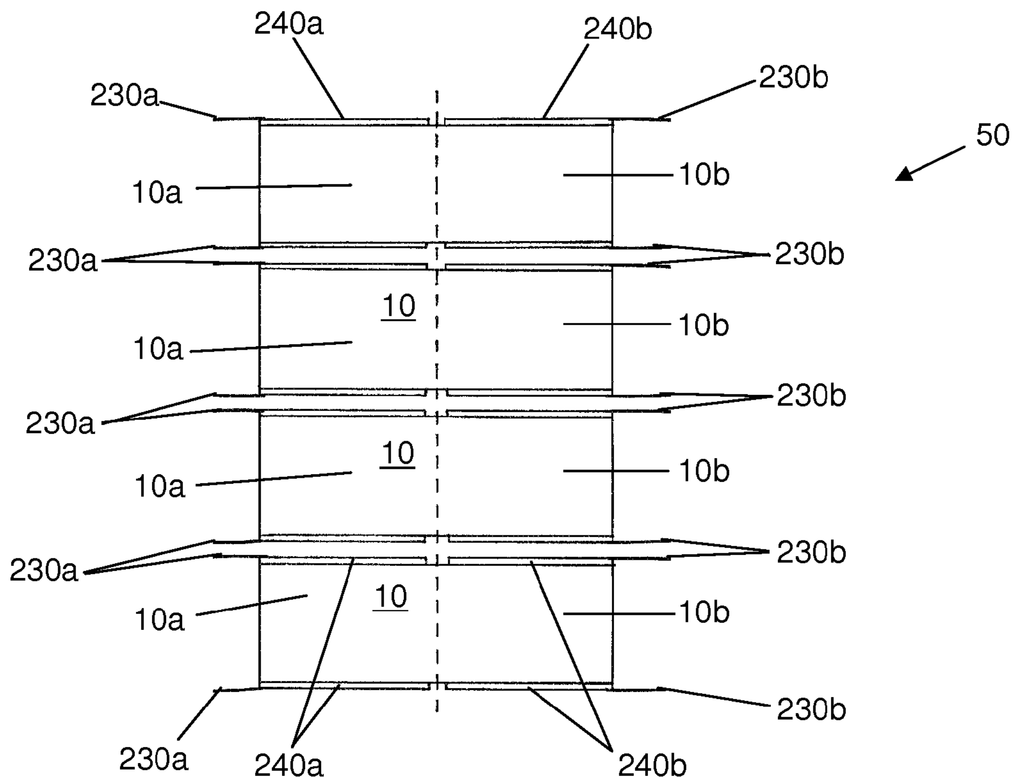
FIG. 3 shows a side view of a plurality of transducer elements configured in accordance with one aspect of the present invention.

Turning now to FIG. 3, there is shown a slightly exploded side view of a transducer stack 50 formed in accordance with the principles of the present invention. The transducer elements 10 have been formed so as to have electrically isolated portions 10*a* and 10*b*. A plurality of electrodes 240*a*, 240*b*, and electrical leads 230*a*, 230*b* are used to independently apply electricity to the portions 10*a* and 10*b* of the transducer elements 10. By electrically stimulating portions of the transducer elements out of phase with other portions, flexural motion can be induced in a horn (as shown in FIG. 1) which is connected to the stack. Thus, for example, all of the portions 10*a* could have a voltage applied which caused these portions of the transducer elements to expand, while all of the portions 10*b* simultaneously have the opposite polarity of voltage applied so as to cause those portions of the transducer elements to contract. This would cause expansion on the left side of the stack and contraction on the right. The expansion and contraction would cause the horn to bend to the right of the axis A-A, thereby providing flexural and transverse motion. By selectively expanding some of the portions and contracting others, the horn can be driven in both longitudinal and flexural motions. This can be achieved, for example, by expanding the first two portions 10*a* and the last two portions 10*b*. By adjusting the ratios and how out of phase the portions expand and contract, the flexural and longitudinal oscillations can be controlled.

It will be appreciated that, depending on the level of control over the motion of the transducer horn and needle, all of the transducer element halves 10*a*, 10*b* may be independently driven, or some or all of the transducer element halves 10*a*, 10*b*, may be wired together and driven together. Thus, some or all of element halves 10*a* may be wired together and some or all of element halves 10*b* may be wired together.

Figure 4:
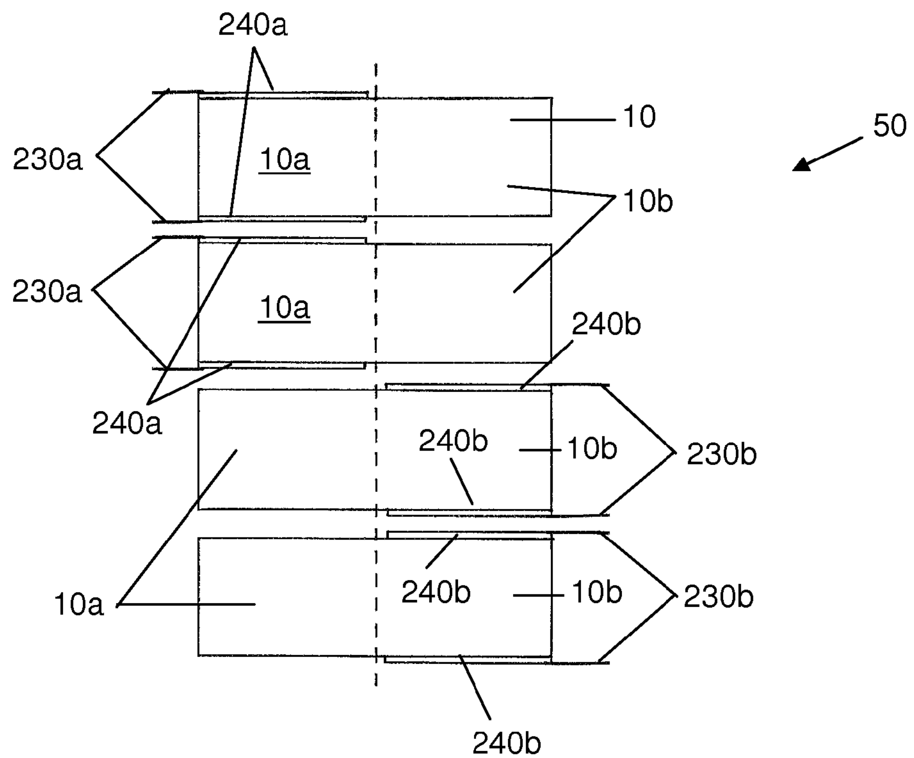
FIG. 4 shows a side view of a plurality of transducer elements configured in accordance with another aspect of the present invention.

Turning to FIG. 4, an alternate configuration of the stack is shown. Rather than electrically isolating portions of the transducer element electrodes 240 as is shown in FIG. 3, the electrodes 240 are disposed on opposing sides of only a portion of transducer element and not on the remainder of the transducer element. Thus, as shown in FIG. 4, the electrodes 240*a*, 240*b* are disposed on the left side of the top two transducer elements 10*a* and on the right side of the lower two transducer elements 10*b*. Applying a voltage to the top two transducer elements 10*b* will cause expansion on the left side, while applying voltage to the bottom two transducer elements 10*a* will cause expansion on the right side (or contraction on those sides with the opposite voltage polarity being applied). The uneven expansion of the transducer elements may be used to create transverse motion in addition to longitudinal motion. By controlling the extent to which the expansion and contraction is out of phase between the different transducer element groups, control is provided to either enhance or minimize longitudinal and flexural motion.

Additionally, the stack may be constructed as is shown in FIG. 3 but driven as is shown in FIG. 4, where only a portion of the transducer element sections 10*a*, 10*b* are driven. These transducer sections are selected based upon the type of motion which is to be produced in the needle tip.

Figure 5:
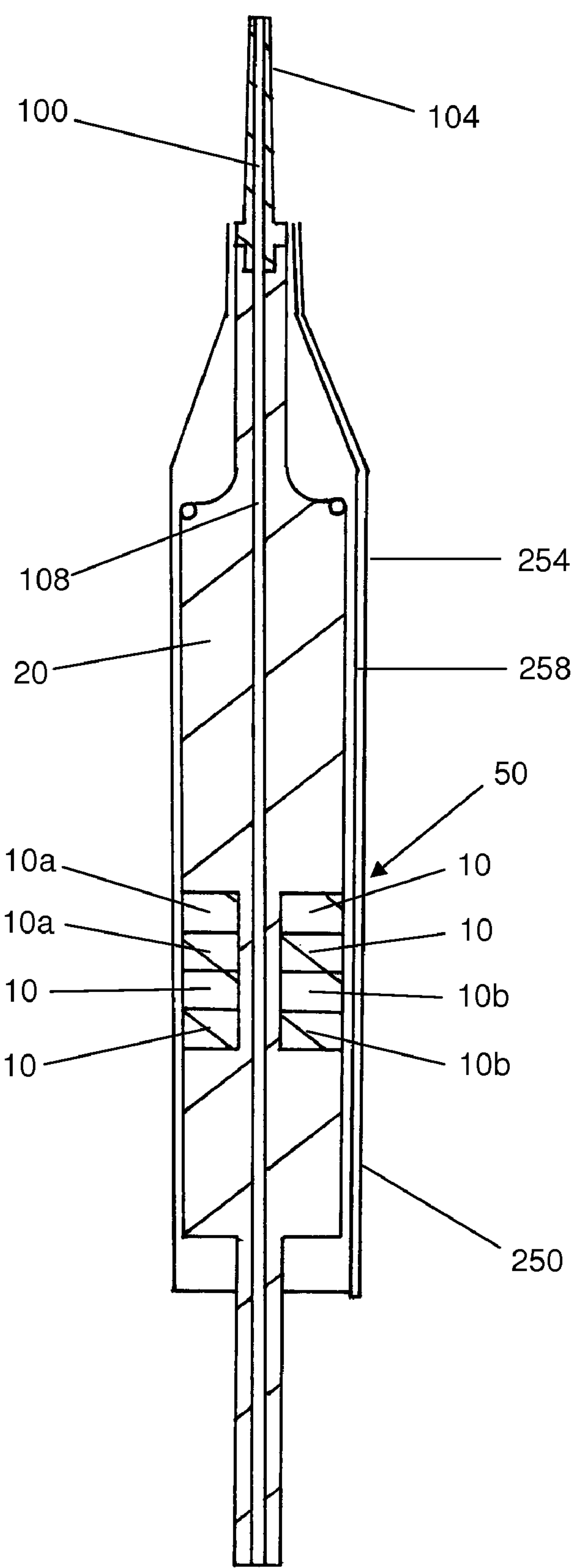
FIG. 5 shows a Langevin transducer assembly formed in accordance with the present invention and disposed inside of a phacoemulsification handpiece.

FIG. 5 shows a cross-sectional view of an ultrasonic hand piece 250. The handpiece includes a body 254 and a horn 20 as are commonly available. The body 254 includes an irrigation channel 258 for irrigating the eye during phacoemulsification. The liquid and emulsified cataract are drawn through the lumen 100 in the needle 104 and on through the channel 108 in the horn 20.

The transducer elements 10 can be configured in either manner discussed with respect to FIGS. 2 through 4. They are driven to create both longitudinal and flexural motion in the horn 20 as is desired. Because they can be formed in substantially the same configuration as a conventional stack of transducer elements, the transducer elements 10 can be used without significant modification to a conventional hand piece 250 or horn 20. Thus, longitudinal and flexural motion can be provided by simply replacing a conventional stack with a stack formed in accordance with the principles of the present invention.

A typical prior art phacoemulsification transducer stack is driven by applying an oscillating voltage to the transducer stack. The transducer elements may all be driven together from the same voltage waveform. According to the present invention, the different segments of the transducer elements may be driven separately to alter the type of motion which is produced by the needle. Thus, control circuitry for a phacoemulsification handpiece of the present invention may include two waveform generators and a control circuit to vary the phase delay between the two produced waveforms. In driving the transducer elements, it will often be the case that different frequencies of wave form will be required to optimally drive the transducer elements in the longitudinal vibration and lateral vibration modes of operation. It is typically desirable to drive the transducer elements at a frequency which is sympathetic to the harmonis frequencies of the horn and needle, and these may have different harmonic frequencies for longitudinal versus lateral vibration. Thus, a simplified control circuit could be made which either drives the transducer elements in phase with each other to produce longitudinal vibration and a first frequency or drives the transducer elements out of phase as discussed to produce lateral vibration using a second different frequency.

Alternatively, the control circuit could have a single waveform generator and a control circuit to separate the waveform signal into two signals and to delay one of the signals relative to the other signal. Thus, according to one embodiment of the invention, one of the resultant waveforms is applied to transducer element portions 10*a* (via electrical leads 230*a* and electrodes 240*a*) and the other resultant waveform is applied to transducer element portion 10*b*. It will be appreciated that some of the above methods of operation, such as a variable phase delay or the same frequency for in phase versus out of phase use, may result in a less efficient driving of the transducer elements. As these modes of operation may result in other advantages, they may still be employed.

Where the ceramic electrodes are segmented into 3 or more isolated conductors, various types of motion may be induced in the needle tip by regulating the phase of the drive signal to the 3 conductors. Various different types of motion other than longitudinal motion may be created, as well as combinations of these motions. The use of multiple isolated electrode segments allows for the creation of different types of motion, as well as the direction and speed the motion. The 3 conductors may be driven at a different frequencies, or with a non-oscillating signals superimposed on the oscillating common mode signal which produces longitudinal motion.

While it has been primarily discussed above that the isolated portions of the transducer elements 10 are driven by out of phase voltage waveforms to create lateral oscillation of the needle tip, these same portions of the transducer element could also be driven by in phase voltage waveforms of differing magnitude to produce lateral vibration of the needle tip. Out of phase waveforms typically produce the maximum amount of lateral vibration in the needle tip and in phase waveforms of differing magnitudes typically produce a mixture of longitudinal and lateral vibration. Thus, a mixture of longitudinal and lateral vibration may be created by driving the transducer element portions with an in phase waveform with a different maximum voltage, and the relative amounts of longitudinal and lateral motion may be controlled by varying the difference in the voltages (amplitudes) of the waveforms applied to the transducer element sections. Thus, different types and combinations of longitudinal and transverse needle motions can be created by using combinations of waveform amplitude, frequency, and phasing and by selectively applying these waveform signals to the individual portions of the ceramic transducer elements.

The person using the phacoemulsification handpiece can adjust the phase angle between the two waveforms via the control circuit. If the phase angle is 0 degrees, the waveforms are aligned in time and the polarity of the voltages applied to the transducer portions 10*a*, 10*b* is the same, resulting in longitudinal movement of the needle tip. If the phase angle is 180 degrees, the two waveforms are completely out of phase such that the voltage polarity applied to transducer elements 10*a* is opposite that applied to transducer elements 10*b*, resulting largely in lateral motion of the needle tip. If the phase angle is between 0 and 180 degrees, a combination of longitudinal and lateral motion is produced.

There is thus disclosed an improved Langevin type transducer that induces flexural/transverse motion along with longitudinal motion, and allows a user to select the type of motion produced at the tip of a phacoemulsification handpiece. It will be appreciated that numerous changes may be made to the present invention without departing from the scope of the claims. The appended claims are intended to cover such modifications.

What is claimed is:

1. An ultrasonic surgical instrument comprising:

a horn body having a working member attached to an end thereof;

a piezoelectric transducer element attached to the horn body such that excitation of the piezoelectric element causes vibration of the working member;

a first pair of electrodes attached to top and bottom sides of a first portion of the transducer element such that the electrodes form an active area on the transducer element which covers the first portion of the transducer element and which does not cover a second portion of the transducer element such that when voltage is applied to said first pair of electrodes said first portion expands differently than said second portion; and a second pair of electrodes attached to the second portion of the transducer element, wherein the first portion and the second portion are electrically isolated from each other.

2. The ultrasonic surgical instrument of claim 1, further comprising a control circuit connected to the first portion and the second portion of the transducer element, the control circuit being configured for applying a first voltage waveform to the first portion and a second voltage waveform different from the first voltage waveform to the second portion such that the first portion expands differently than the second portion.

3. The ultrasonic surgical instrument of claim 2, wherein the first voltage waveform and second voltage waveform are opposite polarity.

4. The ultrasonic surgical instrument of claim 2, wherein the first voltage waveform and second voltage waveform have different voltage magnitudes.

5. The ultrasonic surgical instrument of claim 2, wherein the control circuit allows a user to vary the phase angle between the first voltage waveform and the second voltage waveform.

6. The ultrasonic surgical instrument of claim 2, wherein the first voltage waveform and the second voltage waveform are out of phase with one another.

7. The ultrasonic surgical instrument of claim 2, wherein the control circuit is selectable between a first mode of operation where the first voltage waveform and the second voltage waveform are out of phase and a second mode of operation where the first voltage waveform and the second voltage waveform are in phase.

8. The ultrasonic surgical instrument of claim 7, wherein, in the first mode of operation the first and second waveforms are at a first frequency and in the second mode of operation the first and second waveforms are at a second frequency different than the first frequency.

9. The ultrasonic surgical instrument of claim 1, wherein the first portion and the second portion of the transducer element are disposed on generally opposing halves of the transducer element such that applying out of phase voltages to the first and second portions of the transducer element causes uneven expansion or contraction between the halves of the transducer element.

10. The ultrasonic surgical instrument of claim 1 wherein the instrument comprises a plurality of transducer elements disposed in a series along the horn.

11. The surgical ultrasonic instrument of claim 1, wherein the second portion has a second pair of electrodes attached to top and bottom sides thereof which are electrically insulated from the pair of electrodes attached to the first portion.

12. The ultrasonic surgical instrument of claim 1, wherein the ultrasonic instrument is a phacoemulsification handpiece.

13. The ultrasonic surgical instrument of claim 1, wherein the horn has a needle is attached to one end of the horn and an aspiration tube is attached to an opposing end of the horn.

14. An ultrasonic surgical instrument comprising:

a body;

a horn at least partially disposed in the body;

a piezoelectric transducer disposed adjacent the horn; and a first pair of electrodes attached to the top and bottom of a first part of the piezoelectric transducer so as to form a first active portion, a second pair of electrodes attached to the top and bottom of a second part of the piezoelectric transducer so as to form a second active portion; and wherein the first and second active portions are electrically isolated from one another and electrical signals may be applied thereto independent of one another.

15. The ultrasonic surgical instrument of claim 14, further comprising a control circuit for supplying out of phase voltages to the first and second active portions.

16. The ultrasonic surgical instrument of claim 14, further comprising a second piezoelectric transducer which has first and second electrically isolated active portions defined by first and second electrode pairs attached to top and bottom surfaces of the respective first and second active portions.

17. The ultrasonic surgical instrument of claim 14, wherein the first active portion comprises a first half of the piezoelectric transducer and the second active portion comprises a second half of the piezoelectric transducer.

18. The ultrasonic surgical instrument of claim 14, wherein the piezoelectric transducer comprises a plurality of active regions which are positioned radially about the horn.

19. The ultrasonic surgical instrument of claim 14, wherein out of phase voltages are applied to the first active portion and the second active portion so as to cause uneven expansion in the first and second active portions.

20. The ultrasonic surgical instrument of claim 19, further comprising a control circuit which provides a first voltage waveform to the first active portion and a second different voltage waveform to the second active portion.

21. The ultrasonic surgical instrument of claim 19, wherein the control circuit allows a user to vary the phase angle between the first and second wave voltages.

* * * * *